United States Patent [19]

Richman et al.

[11] 4,454,055

[45] Jun. 12, 1984

[54] ABSORBENT COMPOSITION OF MATTER, PROCESS FOR PREPARING SAME AND ARTICLE PREPARED THEREFROM

[75] Inventors: Edward Richman, Ambler, Pa.; Mark A. Thorn, North Brunswick, N.J.

[73] Assignee: National Starch and Chemical Corporation, Bridgewater, N.J.

[21] Appl. No.: 181,277

[22] Filed: Aug. 25, 1980

[51] Int. Cl.$^3$ ............................................. C09K 3/00
[52] U.S. Cl. ......................................... 252/194; 128/156; 604/368; 128/285; 604/376
[58] Field of Search ................ 252/194; 260/9, 17 R; 128/156, 284, 285; 525/54.24, 54.26, 54.31, 54.32; 524/47, 51, 52; 106/197

[56] References Cited

U.S. PATENT DOCUMENTS

| | | | |
|---|---|---|---|
| 3,935,363 | 1/1976 | Burkholder et al. | 128/284 X |
| 4,043,952 | 8/1977 | Ganslaw et al. | 106/197 C |
| 4,134,863 | 1/1979 | Fanta et al. | 524/602 |
| 4,190,563 | 2/1980 | Bosley et al. | 128/285 |

FOREIGN PATENT DOCUMENTS 1554002 10/1979 United Kingdom .

*Primary Examiner*—Josephine Barr
*Attorney, Agent, or Firm*—Edwin Szala; Margaret Kelley

[57] ABSTRACT

A dry, solid, water-swellable absorbent composition of matter is prepared by blending together (a) a water-insoluble absorbent polymer and (b) from 1 to 75%, by weight of the blend, of an extender material selected from uncrosslinked cellulose derivatives, starch, certain clays and minerals, or mixtures thereof. The composition is characterized by having an absorbency exceeding the sum of the absorbencies, calculated proportionately, of the individual components. In one preferred embodiment, the absorbent polymer is a water-swellable ionic complex of a water-soluble anionic polyelectrolyte and a polyvalent metal cation having a valence of at least three.

21 Claims, No Drawings

ABSORBENT COMPOSITION OF MATTER, PROCESS FOR PREPARING SAME AND ARTICLE PREPARED THEREFROM

BACKGROUND OF THE INVENTION

The present invention relates to an improved composition of matter having absorbent characteristics. In particular, this invention is directed to an improved water-swellable extended absorbent composition of matter, processes for the preparation thereof, and absorbent articles prepared therefrom.

Recently there has been increased activity in the area of water-insoluble particulate hydrocolloid absorbent compositions of matter and products using the same, such as absorbent dressings, diapers, catamenial tampons, and the like for absorbing aqueous fluids such as water, urine, blood and other aqueous body exudates. Such substantially water-insoluble compounds maintain their particulate character as they imbibe and absorb several times their weight of surrounding liquid. In doing so, each individual absorbent particle swells or enlarges several hundred percent its individual perimeter without destruction of its initial particulate integrity. Each particle maintains the approximate shape and geometry it had before contact with liquid, but the dimensions are greatly enlarged to provide for the binding of the liquid absorbed therein. The gelatinous mass of swollen particulate water-insoluble particles defines an aciniform structure since each individual absorbent particle is a greatly enlarged particle, having become liquid-swollen or grape-like or acinus in form due to the liquid it has absorbed. The individual swollen particles are tacky and hence form a clustered mass of liquid-swollen particles. The particles remain in an acinus form state despite the presence of liquid in excess of their ability to absorb. The liquid-swollen particles bind their absorbed water tightly but upon drying they become dehydrated, returning more or less to their original size, and can operate substantially as before to absorb and bind liquids.

The water-insoluble absorbent compositions described above are generally formed in either of two ways. As described in U.S. Pat. Nos. 3,628,534; 3,669,103 and 3,670,731, one or more monomers, which if homopolymerized would form a water-soluble polymer, are copolymerized with a polyfunctional monomer which covalently crosslinks the molecule and introduces a limited water insolubility. In general, the degree of crosslinking is controlled so that the polymer is not soluble in aqueous media, yet remains flexible and swells as the aqueous media is absorbed within its structure.

Alternatively, as described in U.S. Pat. No. 4,090,103, such water-insoluble compositions may be formed through the polymerization and ionic complexing of one or more monomers, which if homopolymerized would form a water-soluble polymer, with polyvalent metal cations having a valence of at least three. The advantage of the ionically complexed compositions over the covalently crosslinked compositions is that the former are easy to shape and apply to substrates for particular applications since they may be uncomplexed and recomplexed by adjusting the pH.

Another class of materials known for their good water-absorbent properties is the polysaccharide graft polymers as described in such patents as U.S. Pat. Nos. 2,922,768 and 4,134,863.

Clay is known for its property of absorbing aqueous liquids; however, its colloidal, dispersive characteristics in water prevent its use in such absorbent materials as tampons or disposable diapers. It is known from U.S. Pat. No. 3,935,363 that clay minerals, when flocculated into granular aggregates using small amounts of an inorganic salt solution and/or a water-soluble polymeric flocculating agent such as polyacrylic acid, and then dried, have enhanced water-absorbing properties. However, the absorbency effect of clay and/or soluble polyelectrolytes when blended with a water-insoluble absorbent material has not been disclosed in the prior art.

U.K. Pat. No. 1,554,002 discloses sanitary articles for absorbing body fluids containing as the absorbent composition a mixture of an acrylic acid polymer salt and guar gum, alginate, xanthan gum or mixtures thereof, but the teaching is limited to these three classes of materials.

Accordingly, it is an object of the present invention to provide an improved dry, solid, water-swellable extended composition of matter which is economical to prepare and which manifests good or dramatically improved absorbent properties.

It is another object to provide processes for preparing such a composition and an absorbent article prepared from the composition.

SUMMARY OF THE INVENTION

The above and related objects are achieved in a dry, solid, water-swellable absorbent composition of matter comprising a blend of:

(a) a water-insoluble absorbent polymer selected from the group consisting of a polysaccharide graft polymer, a covalently crosslinked anionic polyelectrolyte, and an ionically complexed anionic polyelectrolyte; and (b) from about 1 to 75%, by weight of the blend, of an extender material selected from the group consisting of uncrosslinked cellulose derivatives, starch, montmorillonite clay, attapulgite clay, sericite, talc, kaolin, silica, and mixtures thereof, said composition being further defined as having an absorbency which exceeds the sum of the absorbencies, calculated proportionately, of said polymer and said extender material, when measured by blood-saline pressure retention at pressure of 1.0 psi.

As most of the extender materials employed herein are readily available and relatively inexpensive to obtain, they generally provide both a practical and economically attractive means of obtaining adequate absorbency. While all of the extender materials contribute to the water absorbency of the blend, when certain preferred extender materials and absorbent polymers are employed, the absorbency of the resultant blend is synergistically improved.

It is surprising that certain extender materials herein having inherently lower absorbency properties than other materials function better in enhancing the absorbency properties of the blend. For example, it is well known that conventional water-soluble carboxymethyl cellulose in the sodium salt form can be crosslinked with, e.g., epichlorohydrin, or made insoluble by a simple heat treatment to obtain highly absorbent materials; yet, the untreated sodium carboxymethyl cellulose herein performs far better than its crosslinked counterpart as an absorbency enhancer in the blends of this invention.

It is also unexpected, in view of the teachings of U.S. Pat. No. 3,935,363, that if clay, one of the extender materials herein, is added in its natural, unflocculated state to the insoluble polysaccharide graft polymer or polyelectrolyte, it will not dilute, and in preferred aspects will significantly enhance, the absorbency characteristics of the polyelectrolyte.

The absorbent composition herein may be employed in such articles as, e.g., diapers, sanitary napkins, catamenial tampons, dressings, mats, wiping cloths, and any other absorbent articles in which polysaccharide graft polymers or crosslinked or ionically complexed anionic polyelectrolytes may be incorporated.

DESCRIPTION OF THE PREFERRED EMBODIMENTS

The absorbent polymer herein must be substantially or totally insoluble in water for the blend to be an effective absorbent composition. Such a polymer falls within one of three classes: a polysaccharide graft polymer, a covalently crosslinked anionic polyelectrolyte or an ionically complexed anionic polyelectrolyte.

The polysaccharide graft polymer typically consists of a cellulosic, starch or starch-containing backbone on which acrylonitrile or other polymerizable monomers or copolymers are grafted, as taught, e.g., by U.S. Pat. Nos. 2,922,768; 4,045,387; 4,028,290 and 4,134,863. The graft polymers may then be saponified or hydrolyzed to form highly insoluble, absorbent compositions of matter, as disclosed, e.g., by U.S. Pat. Nos. 3,425,971; 3,661,815 and 3,935,099. The term "polysaccharide graft polymers" also includes those polymeric compositions prepared by physically mixing the polysaccharide and polyacrylonitrile or acrylic acid or its salts or other graft monomers or co-polymers, and curing the mixture by either heat or prolonged standing at room temperature, as described in U.S. Pat. No. 4,116,899. The preferred polysaccharide graft polymers herein are starch or starch-containing graft polymers.

The covalently crosslinked anionic polyelectrolytes comprising the second class of water-insoluble absorbent polymers may be formed from water-soluble anionic polyelectrolytes comprising polymers having anionic groups (such as carboxyl, sulfonate, sulfate or phosphate anionic groups) which have been covalently crosslinked to render them water-insoluble, yet water-swellable. Such water-insoluble anionic polyelectrolytes and their preparation are described in detail in the aforementioned U.S. Pat. Nos. 3,628,534, 3,669,103 and 3,670,731. Typically, polyfunctional compounds are copolymerized with the polyelectrolyte monomer or prepolymer so as to enter into a plurality of polyelectrolyte polymer chains or attach to the available dependent functional groups of a plurality of polymer chains. Conventional polymerization techniques, including ultraviolet and other radiation-initiated polymerization mechanisms, may be used. Examples of suitable polyfunctional compounds include divinyl compounds (such as divinyl benzene, divinyl diethylene glycol diether, divinyl diphenyl silane and divinyl sulfone), allyl compounds (such as triallyl cyanurate, trimethylol propane diallyl ether, allyl methacrylate, allyl acrylate, allyl crotonate, diallyl phthalate, diallyl succinate and diallyl sucrose), polyfunctional acrylates and methacrylates (such as tetraethylene glycol diacrylate, triethylene glycol dimethacrylate, pentaerythritol tetraacrylate, ethylidene dimethacrylate and trimethylol propane trimethacrylate), and polyfunctional acrylamides and methacrylamides (such as N,N'methylene bis-acrylamide, and N,N'-methylene bis-methacrylamide, etc.).

The water-insoluble ionically complexed anionic polyelectrolytes comprising the third class of absorbent polymers may be formed from water soluble anionic polyelectrolytes comprising polymers having anionic groups as described above which have been ionically complexed to render them water-insoluble, yet water-swellable. A polyvalent metal cation having a valence of at least three is used to complex the polyelectrolyte to render the overall polymer composite substantially insoluble yet highly swellable in aqueous media such as water, urine, blood, etc. The ionically complexed anionic polyelectrolytes useful herein are described in detail in U.S. Pat. No. 4,090,103, the disclosure of which is incorporated herein by reference.

An absorbent composition of the covalently crosslinked or ionically complexed polyelectrolytes is defined as providing a gelatinous agglomerate of liquid-swollen particulate members in the presence of a quantity of body exudate, as capable of absorbing at least about fifteen times its weight in body exudate, and as capable of retaining the absorbed exudate when exposed to pressure sufficient to deform the agglomerate.

It will be recognized by the practitioner that where a composition is desired having far improved water absorbency than the sum of the relative absorbencies of each component of the blend, only certain of the absorbent polymers herein are effective, depending on the extender material blended therewith, the method of blending and the relative amount of polymer in the total blend. Generally, most of the starch graft polymers and covalently crosslinked anionic polyelectrolytes do not give this improved absorbency effect, and in some cases only certain of the ionically complexed polyelectrolytes are effective. For example, it is known from U.S. Pat. No. 4,043,952, the disclosure of which is incorporated herein by reference, to treat the ionically complexed anionic polyelectrolyte described above so as to provide it with a surface ionically complexed by at least one polyvalent metal cation to improve its aqueous dispersibility or wet-out. In accordance with the present invention it has been found that in certain dry blends of this surface-treated anionic polyelectrolyte and extender material only the blend containing the polyelectrolyte surface-treated with a higher level of cation exhibits dramatically increased absorbency. This is particularly unexpected since the polyelectrolyte surface-treated with a lower cation level typically has higher initial absorbency than the more highly cationically complexed polyelectrolyte. The minimum surface-treatment level of cation necessary to achieve this result cannot be stated with certainty because it varies widely depending on such factors as, for example, the polyelectrolyte (e.g., its molecular weight and extent of neutralization) and the particular cation (e.g., its size and valence). In addition, when the ingredients are wet-blended, the absorbency of the blend is not affected by the level of surface treatment of the polyelectrolyte. Thus, no generalization can be made regarding the minimum or maximum desirable cationic complexing or surface-treatment level, and the practitioner will recognize which ionically complexed polyelectrolytes are effective for this purpose, and also which other absorbent polymers improve absorbency under different conditions. A particularly preferred polyelectrolyte herein is the polyacrylic acid/aluminum cation complex having 40–85% of its carboxylate groups neutralized, prepared by adding the aluminum cation (as aluminum acetate) during precipitation polymerization of the acrylic acid with a free-radical catalyst, so as to provide about 0.3 milliequivalents of aluminum per gram of polymer, which is thereafter surfaced-treated as described in U.S. Pat. No. 4,043,952. A preferred level of surface treatment for this particular polymer in the dry-blended composition is about 0.4 milliequivalents of aluminum per gram of polymer.

In accordance with the present invention the water-insoluble absorbent polymer is blended with an extender material consisting of uncrosslinked cellulose derivatives, starch, selected clays and minerals, or mixtures thereof. Suitable cellulose derivatives herein include, e.g., sodium carboxymethyl cellulose, hydroxyethyl cellulose, methyl cellulose, hydroxypropylmethyl cellulose, and the like. The starches which are applicable herein include certain native starches such as corn or waxy maize starch, cold-water-dispersible starches, which optionally may be crosslinked, such as pregelatinized (e.g., drum-dried or spray-dried) starches, and derivatized starches of a sufficiently high degree of substitution (D.S.) to be dispersible in cold water. Derivatized starches suitable herein include acetylated, carboxylated, carboxymethylated and hydroxypropylated starch. Also within the scope of this invention as extender materials are selected clays, i.e., montmorillonite clay (sodium montmorillonite, or bentonite, in particular), attapulgite clay, as well as the minerals sericite, talc, kaolin and silica. Mixtures of two or more of any of the above extender materials are also suitable herein, and, depending on the material used, may actually be advantageous. It is noted, for example, that montmorillonite and attapulgite clays are particularly effective when used in admixture with another extender material.

All of the extender materials within the scope of this invention have the common characteristic that they must be such as to provide a composition having an absorbency which exceeds the sum of the absorbencies of the individual components, calculated on the basis of the relative proportions of each component in the blend. The absorbencies used for this characterization are measured by the blood-saline pressure retention test at a pressure of 1.0 psi. Thus, each of these materials contributes some absorbency of its own and thereby extends or even enhances the absorbency properties of the polymer in the blend. In contrast, a material falling outside the scope of this invention would have an absorbency equal to or lower than the proportionate sum of the absorbencies of the components. Examples of such unsuitable materials include, for example, underivatized microcrystalline cellulose, crosslinked carboxymethyl cellulose, sand and Fuller's Earth (trademark for a clay consisting of hydrated aluminum and magnesium silicates).

Among the extender materials applicable herein, some perform considerably better than others in extending or improving the absorbency of the composition of this invention. One preferred group of materials herein are those which not only extend the absorbent properties of the blends but contribute dramatically to their absorbency. Even among this group there are degrees of absorbency improvement, which depend on the amounts and type of absorbent polymer being mixed therewith. Thus, at least in some instances, it appears desirable to employ cellulose derivatives which contain carboxyl functionalities and are relatively viscous (i.e., at least about 1000 cps at 1% concentration at 25° C.), but not exceedingly viscous. However, no generalization can be made with respect to all possible combinations of extender material and polymer, because such properties do not conclusively determine which materials will dramatically improve the water absorbency of the blend. In general, however, the most preferred materials to be mixed with the more highly surface-treated ionically complexed polyelectrolytes are sodium carboxymethyl cellulose which is not coarse, having a viscosity of 1500–2500 cps at 25° C. and at 1% concentration and a D.S. of 0.65–0.85, methyl cellulose, finely divided attapulgite clay, mixtures of sodium carboxymethyl cellulose with attapulgite clay or with coarse or fine montmorillonite clay, and cold-water-dispersible waxy maize starch or starch succinate derivative. Preferred extender materials for the ionically complexed polyelectrolytes are montmorillonite clay and sodium carboxymethyl cellulose having a viscosity of 300–600 cps at 25° C. and at 2% concentration. For compositions containing lesser surface-treated polymers (i.e., the polyelectrolyte surface-treated to a level of about 0.2 milliequivalents of aluminum per gram of polymer), sodium carboxymethyl cellulose of 1500–2500 cps as described above, crosslinked starch derivatives, cold-water-dispersible starch succinate derivatives, attapulgite clay and montmorillonite clay are especially preferred, and diatomaceous silica is particularly effective in the wet-blended composition but not in the dry-blended composition.

As to the other absorbent polymers, the preferred extender materials to be employed with the covalently crosslinked anionic polyelectrolyte are attapulgite clay or cold-water-dispersible starch succinate derivatives, which lend to the composition an absorbency much improved over the sum of the absorbencies of the components, taken proportionately. The preferred extender materials for the acrylonitrile starch graft polymers are sodium carboxymethyl cellulose of 1500–2500 cps as described above and attapulgite clay, and for a drum-dried mixture of potassium acrylate and starch the preferred extender is sodium carboxymethyl cellulose of 1500–2500 cps.

That certain of these materials function better than others is surprising in view of the absorbency properties of the pure materials. Thus, it is unexpected that uncrosslinked sodium carboxymethyl cellulose, having poorer absorbency by itself than crosslinked sodium carboxymethyl cellulose (see, e.g., U.S. Pat. No. 3,589,364), functions better to improve absorbency. Also, sodium montmorillonite, a better absorbent clay than attapulgite clay for addition to soluble polyacrylates, does not improve the absorbency of the blend as much as does attapulgite clay. In addition, the minerals closely related to attapulgite and montmorillonite clays such as kaolin and sericite do not contribute nearly as much to the absorbency of the blend. It is not fully understood why the attapulgite clay and/or the above-specified sodium carboxymethyl cellulose, in particular, function in conjunction with the preferred ionically complexed polyelectrolyte to enhance the absorbency of the blend beyond mere addition effects, but further interaction of the polyelectrolyte and its complexed metal ions with the clay or carboxymethyl cellulose may in part be responsible.

The extender materials are employed in amounts which depend mainly on which material is used and on the absorbent polymer employed. Amounts of from about 1 to 75% by weight of the total blend may be utilized, provided only that the resultant blend have the defined absorbency characteristics set forth above. It is to be understood that not all amounts within this range will be operable for all materials. For example, attapulgite clay is an extremely effective extender material at 40% concentration using a surface-treated polyelectrolyte as absorbent polymer but poor at 60%, whereas sodium carboxymethyl cellulose of 1500–2500 cps is effective with the same polymer in amounts exceeding 60% by weight. The practitioner will recognize which amounts will optimize the absorbency of the composition desired for the particular components utilized, and will make adjustments in the amounts when mixtures of extender materials are employed. Preferred amounts of sodium carboxymethyl cellulose of 1500–2500 cps as defined above, when employed with the surface-treated ionically complexed polyelectrolyte, range from about 25 to 70%, and most preferably 40 to 60%, by weight.

In the preparation of the extended absorbent compositions of this invention the absorbent polymer and extender material may be physically blended in dry form (dry-blended) at room temperature until thoroughly mixed. Alternatively, they may be blended in slurry form (wet-blended) in, for example, water, mixtures of alcohol and water, or alcohol alone. The wet blend is then dried by any means desired such as, e.g., by tray, air, oven or drum-drying, and may be dried to a granular form or to a film if a sheet form is desired.

As mentioned above, it is preferred to treat the surface of the ionically complexed polyelectrolyte if it is employed as the absorbent polymer. This may be accomplished either by surface-treatment and drying of the polyelectrolyte before blending with the extender material or by wet-blending the polyelectrolyte and extender material in the presence of polyvalent cations of at least one metal for a period of time sufficient for said cations ionically to complex the outer surface of the composition, which composition is thereafter dried. In the latter case, the preferred extender materials are sodium carboxymethyl cellulose of 1500–2500 cps, attapulgite clay and silica.

The absorbent capacity of the blend herein is independent of its physical dry form, and accordingly the blend may be used as a film, aerated film, powder or fiber. It can be utilized to absorb any aqueous fluid mixture such as water, blood or urine, and is useful in conjunction with other materials to form articles of manufacture (such as absorbent dressings, diapers, sanitary napkins, catamenial tampons, cosmetics, absorbent non-woven fabrics and the like) as well as by itself (as an absorbent body powder, soil additive to maintain moisture anti-perspirant, seed germination aid, pet litter additive to absorb urine, and the like). The composition may be utilized furthermore in articles of manufacture where water absorbency is not the end in and of itself, but merely a means to the end; for example, the absorbent composition may be an ingredient of tablets designed to dissolve rapidly in water or body fluids.

In the examples which follow, all parts and percentages are given by weight and all temperatures in degrees Celsius unless otherwise noted.

BLOOD-SALINE PRESSURE RETENTION TEST

This test is used to evaluate the amount of blood the absorbent sample can retain under pressure.

One gram of the absorbent composition to be tested is placed between two layers of uncoated tissue paper in a Buchner funnel of 70 mm internal diameter and the combined weight of the funnel and its contents is determined and designated A. The outlet of the funnel is stoppered and a test fluid consisting of nine parts of a solution of 0.9% by weight saline in distilled water and one part of whole human blood is added until the absorbent composition is completely covered. The funnel is then fitted to a 500-ml sidearm vacuum filter flask connected to a manometer, the stopper removed after a 5 min. soak and a piece of dental dam rubber sheeting is securely fixed over the mouth of the funnel. A vacuum is then drawn on the flask sufficient to create increasing pressures of 0.5 and 1.0 psi for five minutes at each pressure. The funnel is then removed and weighed (designated B).

The retention under pressure is calculated as follows:

$$\text{Actual Pressure Retention (at 1 psi)} = \frac{B - A}{1\,g} - T_f$$

where $T_f$ is the tissue factor, which has the formula:

$$\frac{B - A}{\text{weight of tissue}},$$

wherein A and B are defined above and the procedure above is employed, except that only the two layers of tissue are used without the absorbent composition placed therebetween. The higher the pressure retention number the greater the absorbency of the composition being tested.

The actual pressure retention value (at 1 psi) is compared in every example with the calculated value (the sum of the absorbencies of each component, taken proportionately), obtained by multiplying the percentage of each component in the blend by its individual absorbency, adding the results together and dividing by 100. For example, if a blend consists of 40% clay and 60% absorbent polymer having respective absorbencies of 15 and 30, the calculated absorbency is $$\frac{(40 \times 15) + (60 \times 30)}{100} = 24.$$

The percent difference between actual and calculated pressure retention values is calculated by the following formula:

$$\frac{\text{actual} - \text{calculated}}{\text{calculated}} \times 100\%$$

The higher this number the more the absorbency of the blend is improved beyond addition effects. If the number is negative, the blend has inferior absorbency and is outside the scope of this invention.

EXAMPLE I

This example illustrates the use of sodium carboxymethyl cellulose in a blend of this invention.

A water-swellable polyacrylic acid/aluminum cation complex containing about 0.3 milliequivalents of aluminum per gram of polymer was prepared by the nonaqueous precipitation polymerization procedure described in U.S. Pat. No. 4,090,013, Example IV (63% of the polymer is neutralized with potassium hydroxide). This polymer was then surface-treated as described in U.S. Pat. No. 4,043,952, Example II in a dispersing medium of 90% methanol/10% water using basic aluminum acetate at a level of about 0.4 milliequivalents of aluminum per gram polymer on a dry basis. The resultant absorbent polyelectrolyte was thereafter dry-blended with the amounts of uncrosslinked sodium carboxymethyl cellulose (having a viscosity of 1500–2500 cps at 25° C. and at 1% concentration and a D.S. of 0.65–0.85) given in Table I. The blood-saline pressure retention test was employed to evaluate the absorbency of each blend, and the results are given in Table I.

TABLE I

| Amount of Sodium Carboxymethyl Cellulose (% by weight of blend) | Blood-Saline Pressure Retention (g/g) | | |
|---|---|---|---|
| | Actual | Calculated | % Difference |
| 0 (control) | 18.6 | — | — |
| 20 | 19.4 | 16.9 | 15 |
| 40 | 31.7 | 15.2 | 109 |
| 60 | 33.2 | 13.3 | 150 |
| 80 | 15.2 | 11.6 | 31 |
| 100 (control) | 9.9 | — | — |

The results indicate that in amounts of between about 25 and 70% by weight of the blend, the carboxymethyl cellulose serves to improve dramatically the water absorbency of the blend beyond mere addition effects.

EXAMPLE II

This example illustrates the preparation of several blends in accordance with this invention and compares their absorbent properties.

The extender materials listed in Table II were dry-blended in the given amounts with the surface-treated polyelectrolyte of Example I. The designation "CMC" in the table is an abbreviation for sodium carboxymethyl cellulose. The absorbent properties of the extender materials and of each blend were tested and are indicated in the table.

TABLE II

| Extender Material | Amount of Extender (% of blend) | Blood-Saline Pressure Retention (g/g) | | |
|---|---|---|---|---|
| | | Actual | Calculated | % Difference |
| None (polyelectrolyte as control)[a] | 0 | 18.6 | — | — |
| Cellulose Derivatives[b]: | | | | |
| CMC (0.65–0.85 D.S., 2500–4500 cps at 25° C. at 1% concentration, medium particle size) | 100[a] | 12.4 | — | — |
| | 40 | 16.9 | 16.2 | 4 |
| CMC (0.65–0.85 D.S, 2500–4500 cps at 25° C. at 1% concentration, coarse particle size having maximum 1% retained on 20 mesh, maximum 50% through 40 mesh and maximum 5% through 80 mesh) | 100[a] | 18.9 | — | — |
| | 40 | 21.5 | 18.7 | 15 |
| CMC (0.65–0.85 D.S., 300–600 cps at 25° C. at 2% concentration) | 100[a] | 5.7 | — | — |
| | 40 | 16.4 | 13.4 | 21 |
| CMC (0.65–0.85 D.S., 25–50 cps at 25° C. at 2% concentration) | 100[a] | 2.5 | — | — |
| | 40 | 12.6 | 12.2 | 3 |
| Crosslinked CMC (sold by Buckeye Cellulose Corporation under U.S. Pat. No. 3,589,364) | 100[a] | 11.3 | — | — |
| | 40[a] | 14.5 | 15.7 | −8 |
| Methylcellulose (3500–5600 cps at 20° C. at 2% concentration) | 100[a] | 2.3 | — | — |
| | 40 | 23.8 | 12.1 | 97 |
| Hydroxyethyl cellulose (1500–2500 cps at 25° C. at 1% concentration, moles of substituent is 2.5) | 100[a] | 14.5 | — | — |
| | 40 | 18.1 | 17.0 | 6 |
| Starches: | | | | |
| Drum-dried starch succinate derivative (sold by National Starch and Chemical Corporation) | 100[a] | 4.0 | — | — |
| | 40 | 16.1 | 12.8 | 26 |
| Spray-dried hydrolyzed starch succinate derivative (60 cps at 15% concentration, sold by National Starch and Chemical Corporation) | 100[a] | 0.1 | — | — |
| | 40[a] | 10.3 | 11.2 | −8 |
| Drum-dried crosslinked hydroxypropyl starch derivative (sold by National Starch and Chemical Corporation) | 100[a] | 10.2 | — | — |
| | 40 | 16.6 | 15.3 | 8 |
| Native waxy maize starch | 100[a] | 1.1 | — | — |
| | 40 | 12.8 | 11.6 | 10 |
| Native corn starch | 100[a] | 0.8 | — | — |
| | 40 | 12.3 | 11.5 | 7 |
| Pregelatinized corn starch | 100[a] | 5.5 | — | — |
| | 40 | 13.5 | 13.4 | 1 |
| Pregelatinized waxy maize starch | 100[a] | 3.9 | — | — |
| | 40 | 17.2 | 12.7 | 34 |
| Inorganic Materials: | | | | |

TABLE II-continued

| Extender Material | Amount of Extender (% of blend) | Blood-Saline Pressure Retention (g/g) | | |
|---|---|---|---|---|
| | | Actual | Calculated | % Difference |
| Attapulgite clay (sold by Engle- | 100[a] | 3.1 | — | — |
| hard Minerals and Chemicals | 60 | 9.5 | 9.3 | 2 |
| Corporation) | 40 | 16.5 | 12.4 | 33 |
| Sodium montmorillonite clay | 100[a] | 2.8 | — | — |
| (granular, 20–160 mesh) | 40 | 14.8 | 12.3 | 20 |
| Sericite (sold by Whittaker | 100[a] | 1.0 | — | — |
| Corp.) | 40 | 12.9 | 11.6 | 11 |
| Talc (sold by Whittaker Corp.) | 100[a] | 1.2 | — | — |
| | 40 | 13.0 | 11.6 | 11 |
| Kaolin (sold by Burgess Pigment | 100[a] | 1.1 | — | — |
| Company) | 40 | 13.0 | 11.6 | 12 |
| Diatomaceous silica (sold by | 100[a] | 2.0 | — | — |
| Witco Chemical Co.) | 40 | 12.7 | 12.0 | 6 |
| Amorphous silica (sold by Imsil | 100[a] | 1.0 | — | — |
| Corporation) | 40 | 13.1 | 11.6 | 12.9 |
| Ottawa sand | 100[a] | 1.6 | — | — |
| | 40[a] | 12.7 | 12.8 | −1 |
| Fuller's Earth (sold by Whittaker | 100[a] | 2.4 | — | — |
| Corporation) | 40[a] | 11.6 | 12.1 | −5 |
| Multi-component: | | | | |
| CMC of Example I and | 25 | 21.0 | 8.8 | 139 |
| Attapulgite clay | 50 | | | |
| Coarse CMC of Example I (having | 100[a] | 31.1 | — | — |
| maximum 1% retained on 20 mesh, | 25[a] | 13.6 | 14.0 | −14 |
| maximum 50% through 40 mesh and | | | | |
| maximum 5% through 80 mesh), and | | | | |
| Attapulgite clay | 50 | | | |
| CMC of Example I and | 25 | | | |
| Sodium montmorillonite clay | 50 | 17.2 | 8.6 | 100 |
| (granular, sold by Georgia- | | | | |
| Kaolin Co.) | | | | |

[a]These examples are for comparison purposes.
[b]Underivatized cellulose yields a negative % Difference value in the pressure retention test of absorbency.

The results indicate that not all extender materials are effective or give equal performance in extending or enhancing the absorbency of the blend. It is noted, moreover, that certain of the extender materials herein dramatically improve the blood-saline pressure retention of the composition of this invention.

EXAMPLE III

This example illustrates the use of other absorbent polymers in preparing the blends of this invention.

Dry blends were prepared by employing the absorbent polymers and extender materials given in Table III, in the indicated amounts. The absorbent properties of the polymers as well as of the blends are given in Table III.

TABLE III

| Blend | Amount of Extender (% of blend) | Blood-Saline Pressure Retention (g/g) | | |
|---|---|---|---|---|
| | | Actual | Calculated | % Difference |
| I. The polyelectrolyte of Example I surface-treated with about 0.2 milliequivalent of aluminum per gram of polymer: | 0[a] | 26.8 | — | — |
| CMC of Example I | 40 | 23.7 | 20.1 | 18 |
| Coarse CMC of Example II | 40 | 28.8 | 28.5 | 1 |
| CMC (0.65–0.85 cps, D.S., 300–600 cps) | 40[a] | 17.4 | 18.4 | −5 |
| Drum-dried crosslinked hydroxypropyl starch derivative | 40 | 22.1 | 20.2 | 9 |
| Drum-dried starch succinate derivative | 40 | 22.0 | 17.7 | 24 |
| Attapulgite clay | 40 | 18.6 | 17.3 | 7 |
| Sodium montmorillonite clay (granular) | 40 | 17.8 | 12.3 | 45 |
| Diatomaceous silica | 40[a] | 15.4 | 16.9 | −9 |
| II. Covalently crosslinked polyacrylic acid (sold by Goodrich Chemical Co.): | 0[a] | 4.3 | — | — |
| CMC of Example I | 40[a] | 5.4 | 6.6 | −18 |
| Attapulgite clay | 40 | 4.8 | 3.8 | 26 |
| Drum-dried starch succinate derivative | 40 | 5.0 | 4.2 | 19 |
| III. Partially neutralized salt | 0[a] | 37.0 | — | — |

TABLE III-continued

| Blend | Amount of Extender (% of blend) | Blood-Saline Pressure Retention (g/g) | | |
|---|---|---|---|---|
| | | Actual | Calculated | % Difference |
| of a saponified starch acrylonitrile graft copolymer (sold by General Mills, Inc.): | | | | |
| CMC of Example I | 40[a] | 19.1 | 26.2 | −27 |
| Attapulgite clay | 40[a] | 22.2 | 23.4 | −5 |
| IV. Drum-dried mixture of potassium acrylate and starch (sold by Staley Manufacturing Co.): | 0[a] | 21.0 | — | — |
| CMC of Example I | 40 | 18.3 | 16.6 | 10 |
| V. Drum-dried acrylic acid starch graft polymer partially neutralized with sodium hydroxide (sold by Sanyo Chemical Co.): | 0[a] | 35.3 | — | — |
| CMC of Example I | 40[a] | 22.4 | 25.2 | −11 |
| VI. Acrylonitrile starch graft polymer (sold by Unilever Ltd.): | 0[a] | 10.8 | — | — |
| CMC of Example I | 40 | 11.9 | 10.5 | 13 |
| Attapulgite clay | 40 | 7.4 | 7.7 | 4 |
| Drum-dried starch succinate derivative | 40[a] | 8.1 | 8.1 | 0 |

[a]These examples are for comparison purposes.

It can be seen that the extender materials are also not equally effective using other absorbent polymers.

EXAMPLE IV

This example illustrates wet mixing of the polymer and extender material to form the composition of this invention. Blends A–E of Table IV were prepared by mixing the ionically complexed anionic polyelectrolyte designated as I in Example III in the indicated amounts with the given extender material in a slurry of 85:15 methanol:water. Each slurry, except E, was then treated as described in U.S. Pat. No. 4,043,952, Example II with basic aluminum acetate to obtain a total surface treatment of about 0.4 milliequivalents of aluminum per gram of polymer, and drum-dried. The absorbency of each blend was evaluated and is indicated in Table IV.

TABLE IV

| Blend | Extender Material | Amount of Extender (% of blend) | Blood-Saline Pressure Retention (g/g) | | |
|---|---|---|---|---|---|
| | | | Actual | Calculated | % Difference |
| Polyelectrolyte (0.4 milliequivalents of Al) | | 0[a] | 18.6 | — | — |
| A | CMC of Example I | 40 | 33.7 | 15.1 | 90 |
| B | Coarse CMC of Example II | 40[a] | 21.6 | 23.6 | −8 |
| C | Attapulgite clay | 40 | 15.9 | 12.4 | 28 |
| D | CMC of Example I and Attapulgite clay | 25 50 | 22.0 | 8.7 | 153 |
| Polyelectrolyte (0.2 milliequivalents of Al) | | 0[a] | 26.8 | — | — |
| E | Diatomaceous silica | 35 | 25.0 | 18.1 | 38 |

[a]These examples are for comparison purposes.

The results show that wet-blending of the ingredients is also an effective means for preparing the absorbent composition of matter herein.

EXAMPLE V

The procedure of Example I was carried out except that the polyelectrolyte was not surface-treated. The absorbency of the resultant blend is given below:

| Amount of Extender (% of blend) | Blood-Saline Pressure Retention (g/g) | | |
|---|---|---|---|
| | Actual | Calculated | % Difference |
| 0[a] | 14.2 | — | — |
| 40 | 14.9 | 12.5 | 19 |

[a]For comparison purposes.

In summary, the present invention is seen to provide a dry, solid water-swellable absorbent composition of matter which is economical to prepare and has good or significantly improved absorbent properties.

Now that the preferred embodiments of the invention have been described in detail, various modifications and improvements thereon will become readily apparent to those skilled in the art. Accordingly, the spirit and scope of the present invention are to be limited only by the appended claims, and not by the foregoing specification.

What is claimed is:

1. A dry, solid, water-swellable absorbent/extender blend, characterized by the improved absorbency of the blend, which comprises:
    (a) an ionically complexed anionic polyelectrolyte which is a water-insoluble ionic complex of a water-soluble anionic polyelectrolyte and a polyvalent metal cation having a valence of at least three; and (b) from about 1–80%, by weight of the blend, of a cellulosic, starch, or inorganic extender, the cellulosic being selected from the group consisting of uncrosslinked sodium carboxymethyl cellulose, methyl cellulose, and hydroxyethyl cellulose; the starch extender being selected from the group consisting of native waxy maize starch, native corn starch, pregelatinized waxy maize starch, pregelatinized corn starch, drum-dried starch succinate, and drum-dried crosslinked hydroxypropyl starch; the inorganic extender being selected from the group consisting of attapulgite clay, sodium montmorillonite clay, seracite, talc, kaolin, diatomaceous silica, and amorphous silica; the absorbency exceeding the sum of the absorbencies, calculated proportionately, of the polyelectrolyte and the extender, when measured by blood-saline pressure retention at pressure of 1.0 psi. and wherein the improvement in the absorbency is at least about 7%.

2. A process for preparing the composition of matter of claim 1 comprising dry-blending said absorbent polymer with said extender material.

3. A process for preparing the composition of matter of claim 1 comprising wet-blending said absorbent polymer with said extender material and drying said wet blend.

4. The process of claim 3 wherein said absorbent polymer is a water-swellable ionic complex of a water-soluble anionic polyelectrolyte and a polyvalent metal cation having a valence of at least three, and wherein polyvalent cations of at least one metal are present in said wet blend for a period of time sufficient for said cations ionically to complex the outer surface of said composition of matter.

5. An article for absorbing bodily fluids containing the composition of matter of claim 1.

6. The composition of claim 1, wherein the polyelectrolyte is polyacrylic acid having 40–85% of its carboxylate groups neutralized and ionically complexed with aluminum.

7. The composition of claim 6, wherein the cellulosic extender is uncrosslinked sodium carboxymethyl cellulose having a viscosity of about 1500–2500 cps. at 25° C. at 1% concentration and a D.S. of about 0.65–0.85, or methyl cellulose; the starch extender is native or pregelatinized waxy maize starch or the starch succinate; and the inorganic extender is attapulgite or sodium montmorillonite clay, sericite, talc, kaolin, or diatomaceous or amorphous silica; wherein the improvement in the absorbency is at least about 10%.

8. The composition of claim 6, wherein the extender is about 40% of the uncrosslinked sodium carboxymethyl cellulose having a viscosity of about 1500–2500 cps. at 25° C. at 1% concentration and a D.S. of about 0.65–0.85; wherein the improvement in the absorbency is at least about 19%.

9. The composition of claim 6, wherein the polyelectrolyte is surface treated at a level of about 0.2 milliequivalents of aluminum per gram of polyelectrolyte.

10. The composition of claim 9, wherein the extender is about 40% of uncrosslinked sodium carboxymethyl cellulose having a viscosity of about 1500–2500 cps. at 25° C. at 1% concentration and a D.S. of about 0.65–0.85; wherein the improvement in the absorbency is at least about 18%.

11. The composition of claim 9, wherein the extender is about 40% of the starch succinate; wherein the improvement in the absorbency is about 24%.

12. The composition of claim 9, wherein the extender is about 40% of attapulgite clay or sodium montmorillonite clay; wherein the improvement in the absorbency is at least about 7% and 45%, respectively.

13. The composition of claim 6, wherein the polyelectrolyte is surface treated at a level of about 0.4 milliequivalents of aluminum per gram of polyelectrolyte.

14. The composition of claim 13, wherein the extender is about 20–80% of uncrosslinked sodium carboxymethyl cellulose having a viscosity of about 1500–2500 cps. at 25° C. at 1% concentration and a D.S. of about 0.65–0.85; wherein the improvement in the absorbency is at least about 15–150%.

15. The composition of claim 13, wherein the extender is about 40% of uncrosslinked sodium carboxymethyl cellulose having a viscosity of about 300–600 cps. at 25° C. at 2% concentration and a D.S. of about 0.65–0.85; wherein the improvement in the absorbency is at least about 21%.

16. The composition of claim 13, wherein the extender is about 40% of native waxy maize starch, pregelatinized waxy maize starch, or drum-dried starch succinate; wherein the improvement in the absorbency is about 10–34%.

17. The composition of claim 13, wherein the extender is about 40% of sodium montmorillonite clay, sericite, talc, kaolin, or amorphous silica; wherein the improvement in the absorbency is at least about 11–33%.

18. The composition of claim 13, wherein the extender is about 40% of attapulgite clay; wherein the improvement in the absorbency is at least about 33%.

19. The composition of claim 13, wherein the extender is about 75% of a 1:2 mixture of an uncrosslinked sodium carboxymethyl cellulose having a viscosity of about 1500–2500 cps. at 25° C. at 1% concentration and a D.S. of about 0.65–0.85 and attapulgite clay or sodium montmorillonite clay; wherein the improvement in the absorbencies is at least about 139% and 100%, respectively.

20. The composition of claim 4, wherein the cation is aluminum.

21. The composition of claim 20, wherein the cellulosic extender is about 40% of an uncrosslinked sodium carboxymethyl cellulose having a viscosity of about 1500–2500 cps. at 25° C. at 1% concentration and a D.S. of about 0.65–0.85; or wherein the inorganic extender is about 40% of attapulgite clay or wherein the inorganic extender is about 40% of diatomaceous silica; or wherein the mixed cellulosic-inorganic extender is about 75% of a 1:2 mixture of the uncrosslinked sodium carboxymethyl cellulose having the 1500–2500 cps. viscosity and the attapulgite clay; wherein the improvement in the absorbencies is at least about 90%, 28%, 38% and 153%, respectively.

* * * * *